United States Patent [19]

Rubino

[11] 4,017,599

[45] Apr. 12, 1977

[54] ALUMINUM-ZIRCONIUM ANTI-PERSPIRANT SYSTEMS WITH SALTS OF AMINO ACIDS

[75] Inventor: Andrew M. Rubino, New Providence, N.J.

[73] Assignee: Armour Pharmaceutical Company, Phoenix, Ariz.

[22] Filed: Nov. 23, 1973

[21] Appl. No.: 418,712

[52] U.S. Cl. .............................. 424/47; 260/429.3; 424/66

[51] Int. Cl.$^2$ ......................................... A61K 7/34

[58] Field of Search ...................... 424/47, 65, 66; 260/448 R, 429.3

[56] References Cited

UNITED STATES PATENTS

| | | | |
|---|---|---|---|
| 2,236,387 | 3/1941 | Wallace, Jr. et al. | 424/68 |
| 2,814,584 | 11/1957 | Daley | 424/66 |
| 2,814,585 | 11/1957 | Daley | 424/66 |
| 2,854,382 | 9/1958 | Grad | 424/68 |
| 3,407,254 | 10/1968 | Siegal et al. | 424/66 |
| 3,792,068 | 2/1974 | Luedders et al. | 424/47 X |

Primary Examiner—Helen M. S. Sneed
Attorney, Agent, or Firm—Frank T. Barber; William W. Schwarze

[57] ABSTRACT

Anti-perspirant complexes are provided which comprise a combination of a basic aluminum compound, a zirconium compound and an amino compound which may be an alkaline or hydroxy salt of an amino acid in which the number of amino groups is equal to the number of carboxyl groups in the molecule. The various components are present in the complex in amounts such that the Al/Zr mol ratio is about 10:1 to 1:10 and the pH of an aqueous solution containing 5 to 15 weight percent of the complex (based on the oxides of aluminum and zirconium) is at least about 3. The basic aluminum compound may be any of the usual basic aluminum anti-perspirant salts, particularly the basic aluminum halides, and the zirconium compound may be a zirconium oxy salt and/or zirconium hydroxy salt. The amino salts may be soluble or insoluble, and particularly preferred compounds include the alkaline and alkaline earth glycinates, aluminum dihydroxy or monohydroxy glycinates, and aluminum-magnesium-hydroxy-glycinate compounds. The complexes may be used in conventional anti-perspirant forms, including aqueous solutions, aerosol sprays (including powder-in-oil aerosol sprays), as well as creams, lotions and cream sticks.

20 Claims, No Drawings

ALUMINUM-ZIRCONIUM ANTI-PERSPIRANT SYSTEMS WITH SALTS OF AMINO ACIDS

BACKGROUND OF THE INVENTION

The present invention relates to aluminum-zirconium anti-perspirant systems with salts of amino acids. More particularly, the invention is directed to water soluble complexes of zirconium which have a sufficiently high pH to be acceptable in anti-perspirant formulations for application to the human axilla.

It has been known in the art for some time that zirconium salts provide exceptionally effective anti-perspirant properties. Such zirconium compounds have included particularly the acidic zirconium salts, such as zirconium oxy chloride or zirconyl chloride, zirconium hydroxy chloride, and other halide and sulfate substitutes of the salts. However, the zirconium salts are extremely acidic and irritating to the skin. For example, a solution of zirconyl chloride which is effective as an anti-perspirant has a pH of only about 0.8 and a solution of zirconyl hydroxy chloride which is effective as an anti-perspirant has a pH of only about 1.2 As a result, it is necessary to buffer these solutions up to a pH of only about 1.2. As a result, it is necessary to buffer these solutions up to a pH which is suitable for application to the human skin, i.e., up to at least about 3 to 5.

A number of prior attempts have been made in the art to buffer solutions of zirconium salts or to form zirconium complexes which take advantage of the effectiveness of zirconium compounds. One early attempt included the development of sodium zirconium lactate for use in cologne-stick type formulations. This lactate complex salt was sufficiently alkaline (pH 8.5), but was ineffective as an anti-perspirant, and was repeatedly implicated in the generation of "zirconium granulomas" in some users.

Other attempts to make use of the acidic zirconium salts involved the buffering of solutions of these salts with urea (see U.S. Pat. No. 2,814,584 to Daley) or water soluble amino acids (see U.S. Pat. Nos. 2,814,585 to Daley and 2,854,382 to Grad) or aliminum hydroxy halides (see U.S. Pat. No. 2,906,668 to Beekman).

More recently, various derivatives have been formed incorporating zirconium compounds, including the amine-amide derivatives of U.S. Pat. No. 3,407,254 to Siegal et al., and the polyhydroxy derivatives of U.S. Pat. No. 3,405,153 to Jones and Rubino.

While the above attempts have succeeded in varying degrees in alleviating the acidic characteristics of zirconium salts, an entirely satisfactory zirconium anti-perspirant composition has not been previously found. Thus, it is desired to find a zirconium anti-perspirant composition which effectively makes use of the exceptional anti-perspirant properties of the zirconium, while at the same time offsetting the acidity and other disadvantages of zirconium salts.

SUMMARY OF THE INVENTION

According to the present invention, it has been found that effective anti-perspirant compositions may be achieved by forming a water soluble complex which comprises a combination of a basic aluminum compound, a zirconium compound selected from zirconium oxy salts, zirconium hydroxy salts and mixtures thereof, and an amino compound selected from alkaline and hydroxy salts of amino acids. These compounds should be present in the complex in such amounts as to yield an Al/Zr mol ratio of about 10:1 to 1:10, and preferably about 1:1 to 4:1, and should be such as to yield a pH of at least about 3 when the complex is placed in aqueous solution in an amount such that the solution contains about 5 to 15 weight percent of zirconium plus aluminum, calculated as the oxides.

The astringent complexes of the present invention may be obtained in solution or dry powder form. As a result, the complexes are satisfactory for use in any of the wide variety of conventional anti-perspirant forms, including lotions, creams, roll-ons, hydro-alcoholic aerosol sprays, and the presently popular powder-in-oil sprays.

DETAILED DESCRIPTION OF PREFERRED EMBODIMENTS

The basic aluminum compounds which may be used in forming the complexes of the present invention include the conventional basic aluminum salts which have been known to the anti-perspirant art for some time, and which have a degree of anti-perspirant efficacy in their own right, as a result of the presence of the active aluminum ion. These basic aluminum salts may be represented by the following general empirical formula:

$$Al_2(OH)_{6-nx}A_x$$

wherein $x$ may vary from greater than 0 to less than 6, $6-nx$ is greater than or equal to 0, $n$ is the valence of A, and A is selected from the group consisting of halides, nitrate, sulfamate, sulfate and mixtures thereof.

It will of course be understood that the above formula is greatly simplified and is intended to represent and include basic aluminum compounds containing coordinated and/or bound molecules of water as well as polymers, complexes and mixtures of the above basic formula.

Particularly preferred basic aluminum compounds of the above formula are the ⅔ to 5/6 basic aluminum chlorides, in which A is chloride and $x$ is between about 1 to 2 and need not be an integer. Thus, such basic aluminum chlorides may be represented by the formulas

$$Al_2(OH)_5Cl \text{ and } Al_2(OH)_4Cl_2.$$

The basic aluminum chlorides are also referred to as aluminum chlorhydroxide or aluminum chlorhydrate or aluminum hydroxy chloride, and are commercially available from Reheis Chemical Company, Division of Armour Pharmaceutical Company under the trademark "Chlorhydrol."

In addition to the simple basic aluminum salts indicated above, complexes or derivatives of the basic aluminum salts may also be used advantageously in the complexes of the present invention. Examples of such derivatives or complexes include the phenolsulfonate derivatives described in U.S. Pat. No. 3,634,480 to Sheffield. Such complexes are formed by reacting 5/6 basic aluminum chloride with phenolsulfonic acid, zinc phenolsulfonate or aluminum phenolsulfonate. Other suitable derivatives and complexes of basic aluminum salts which may be used in the complexes of the present invention will be readily apparent to those of ordinary skill in the art in view of the present specification.

The zirconium compounds which are useful in forming the complexes of the present invention include both the zirconium oxy salts and zirconium hydroxy salts, also referred to as the zirconyl salts and zirconyl hydroxy salts. These compounds may be represented by the following general empirical formula:

$$ZrO(OH)_{2-nz} B_z$$

wherein z may vary from about 0.9 to 2 and need not be an integer, $n$ is the valence of B, $2-nz$ is greater than or equal to 0, and B may be the same as A in the previous formula, that is B may be selected from the group consisting of halides, nitrate, sulfamate, sulfate and mixtures thereof. Although only zirconium compounds are exemplified in this specification, it will be understood that other Groups IV B metals, including hafnium could be used to form the complexes of the present invention.

As with the basic aluminum compounds, it will be understood that the above formula is greatly simplified and is intended to represent and include compounds having coordinated and/or bound water in various quantities, as well as polymers, mixtures and complexes of the above. As will be seen from the above formula, the zirconium hydroxy salts actually represent a range of compounds having various amount of the hydroxyl group, varying from about 1.1 to only slightly greater than 0 groups per molecule.

Particularly preferred zirconium compounds for use in the present invention include zirconyl chloride (also referred to as basic zirconium chloride or zirconium oxy chloride) and zirconyl hydroxy chloride, which may be represented by the simple formulas $ZrO Cl_2$ and $Zro(OH)Cl$, respectively. These compounds are commercially available in solution form. In the alternative, the zirconium compounds can be made by dissolution of commercially available zirconium carbonate paste (carbonated hydrous zirconia) in the appropriate amount of the acid of the anion to be used, e.g. hydrochloric acid.

The amino compounds useful in preparing the complexes of the present invention include both alkaline and hydroxy salts of amino acids. It is important to note that insoluble as well as soluble salts may be used, in contradistinction to the teachings of U.S. Pat. Nos. 2,814,585 and 2,854,382 to Daley and Grad, respectively, which indicte that only amino acids which are sufficiently soluble in aqueous solution can be used to buffer zirconium anti-perspirant solutions. This phenomenon may be accounted for the the belief that the salts of amino acids, even if insoluble in water, form complexes with the zirconium compounds and basic aluminum compounds, which complexes are soluble in water. Moreover, since the complexes of the present invention may be dried to a solid powder form, it is not necessary that the complexes of the present invention be stable in aqueous solution for any great length of time, except when it is desired to redissolve the powder for use in solution form.

Among the salts of amino acids which may be used in the present invention are those derived from the so-called neutral amino acids, i.e., amino acids in which the number of amino groups is equal to the number of carboxyl groups in the molecule. Examples of such amino acids include glycine, DL-valine, β-alanine, arginine and L-(-)-proline and mixtures thereof. The corresponding salts are the glycinates, DL-valinates, β-alaninates, argininates and L-(-)-prolinates. Suitable salts of other amino acids useful in the present invention will be evident to those of ordinary skill in the art in view of this specification.

The particular salts of amino acids which may be used include both alkaline and hydroxy salts. As used herein, the term "alkaline" as applied to salts of amino acids is not intended to be limited to those having a pH greater than 7.0, since some complex or not perfectly neutralized salts may have pH's less than 7.0 (e.g., 6.0 or 6.5) and still be useful in this invention. Instead, alkaline is merely meant to refer to the usual alkali and alkaline earth cations, including ammonium. For example, suitable alkaline salts include sodium, potassium, ammonium, magnesium and calcium salts of the above-mentioned amino acids. These salts may be obtained commercially or prepared by reacting the particular amino acid in aqueous solution with the carbonate or hydroxide of the particular alkali or alkaline earth metal.

Suitable hydroxy salts of amino acids which may be used in the present invention include the dihydroxy and monohydroxy aluminum salts of amino acids and the so-calljed aluminum-magnesium-hydroxy-glycine compounds. Essentially, these hydroxy salts are the reaction products of aluminum hydroxy antacids with the appropriate amino salt. For example, the dihydroxy and monohydroxy aluminum salts may be obtained commercially or prepared by reacting the amino acid with aluminum hydroxide ($Al(OH)_3$) powder in aqueous solution with agitation.

Similarly, the desired amino acid may be reacted with the glycine stabilized aluminum hydroxide-magnesium antacid compositions described in U.S. Pat. No. 3,208,906 to Beekman. For convenience, these antacids will be referred to as aluminum-magnesium-hydroxy-glycine compounds. Examples of such compounds, all of which are insoluble in water, include the following:

AL(OH)$_3$—Mg(OH)$_2$ — glycine
Al(OH)$_3$—Mg CO$_3$ — glycine
AL(OH)$_3$—MG SI$_3$ O$_8$ — glycine Particularly preferred amino compounds for use in the present invention include dihydroxy aluminum glycinate (Al(OH)$_2$ OOC.CH$_2$.NH$_2$, monohydroxy aluminum glycinate (Al(OH)(OOC.CH$_2$.NH$_2$)$_2$, which are commercially available from Chattem Chemical Co. and K and K Laboratories, Inc., as well as magnesium glycinate (Mg(OOC.CH$_2$.NH$_2$)$_2$) and calcium glycinate (Ca(OOC.CH$_2$NH$_2$)$_2$). Commercial glycinates of the above form are available in a large range of different basicities. Accordingly, the amount of glycinate or other salt of amino acid which is necessary to form a complex having a pH in aqueous solution of at least about 3 will depend upon the particular basicity of the amino salt.

The particular amounts of each of the compounds to be added to form the complexes of the present invention may vary over a large range, depend upon the particular properties desired.

In general, the relative amounts of basic aluminum compound and zirconium compound to be added should be such as to yield an Al/Zr mol ratio of between about 10:1 and 1:10, and preferably about 1:1 to 4:1. Although greater amounts of zirconium would be desirable in the complex from the standpoint of antiperspirant efficacy, it will be appreciated that zirconium is considerably more expensive than aluminum.

In addition, the greater the amounts of zirconium in the complex, the greater the chance of skin irritation, and the greater the amount of the amino compound which must be added to obtain a satisfactory pH.

The amount of the amino compound to be added will also vary greatly depending upon the Al/Zr ratio, the particular amino compound used, and the pH range which is desired for the particular astringent complex. In general, sufficient amino compound should be added so that the pH of an aqueous solution of the complex at the normal concentrations for anti-perspirant use will be at least about 3, and preferably in the range of about 3 to 5. The usual concentration of the complexes of the present invention for anti-perspirant use will be such that a solution contains a total aluminum plus zirconium concentration of about 5 to 15 weight percent, with the aluminum and zirconium being calculated as the oxides (i.e., $ZrO_2$ and $Al_2O_3$).

If desired, the pH or the concentration of aluminum in the complexes of the present invention may be adjusted by adding aluminum chloride ($AlCl_3$) to the reaction mixture in the formation of the complexes of the present invention. Aluminum chloride, although quite acidic in solution, is well known for its anti-perspirant efficacy.

The method of forming the complexes of the present invention is not particularly critical. In general, the complexes may be formed simply by adding the various components together in an aqueous solution and then if desired, drying the solution to a dry powder. The various components are preferably added one at a time with stirring, and moderate heating, such as to a maximum of about 75° or 85° C. for up to a half hour may be advantageous after addition of certain ingredients, particularly when an insoluble compound is added or when a precipitate is formed after the addition of an ingredient. Where a water insoluble amino compound is being used, it is preferable to add this last.

The drying step is not particularly critical and may be carried out in a number of different ways, including vacuum drying, oven drying, spray drying or freeze drying. It will be understood that drying does not mean that all of the water is removed, since a certain amount of water should remain in the complex as coordinated and/or bound water. Thus, drying to just past the point where the solution becomes friable solid should be sufficient. If the complex is over dried, so that some of the coordinated and/or bound water is removed, the stability and/or activity of the complex may be interferred with, and the complex may not be readily redissolvable in solvents, particularly hydroalcoholic solvents.

While it has been indicated that the reaction process is not considered particularly critical, it will be understood that sufficient time, heat and agitation are needed to allow reaction of the salts to form the new complexes of the present invention. This is particularly so in the case of insoluble amino acid salts which may be used to form complexes of this invention. Although I do not wish to be bound by any particular theory, it is believed that there is a continuation of the reaction during the drying of the solution to a solid powder. Thus, the pH of a reconstituted solution is often higher than might otherwise be expected from the pH of the solution before drying, even taking into consideration different solution concentrations.

The complexes of the present invention will now be illustrated in more detail with reference to the following specific, non-limiting examples:

EXAMPLE I

Dihydroxyaluminum glycinate [$Al(OH)_2$ glycinate] was prepared by reacting 4 grams with 5 grams of aluminum hydroxide powder (28.8% Al) in 50 grams of water with agitation. The mixture was heated at 75° C. for 30 minutes. After cooling 77 grams of 30% zirconyl chloride (13.6% Zr) was added with stirring. This mixture was heated at 50° C. for 15 minutes. The resultant clear solution was then added to 75 grams of 50% aluminum chlorhydrate (basic aluminum chloride), $Al_2(OH)_5Cl$ (12.5% Al) with agitation and then dried at 50° C. under a vacuum of 303 mm of Hg. The dried product contained 13.6% Al, 11.9% Zr, 4.5% glycine, and 23.3% Cl.

EXAMPLE II

Monohydroxyaluminum glycinate [$Al(OH)(glycinate)_2$] was prepared by reacting 4 grams of glycine with 2.5 grams of aluminum hydroxide powder (28.8% Al) in 30 grams of water. The mixture was heated at 80° C. for one half hour with agitation. The slurry was allowed to cool before adding 200 grams of 33⅓ % zirconyl hydrochloride, $ZrO(OH)Cl$ (14.1% Zr). The mixture was heated at 75° C. for 30 minutes. The resultant clear solution was then mixed with 4.14 grams of 50% aluminum chlorhydroxide (basic aluminum chloride), (12.5%). The product was oven dried at 45° C. under a vacuum of 175 mm of Hg, and found to contain 1.9% Al, 43.9% Zr, 5.1% glycine and 17.6% Cl.

EXAMPLE III

Dihydroxyaluminum glycinate was prepared by reacting 30 grams of aluminum hydroxide gels available from Reheis Chemical Company under trademark F-1000 (aluminum basic carbonate compressed gel), (5.29% Al) with 4.41 grams of glycine with vigorous agitation. The slurry was stirred for 15 minutes at 65° C. and then cooled. Fifty grams of 3⅓% zirconyl hydroxychloride (14.1% Zr) was added to the above slurry. The mixture was stirred and heated at 75° C. until a clear solution resulted. Seventy grams of 50% aluminum chlorhydroxide (12.8% Al) was then added to the above solution with agitation. The solution was evaporated at 55° C. under a vacuum of 303 mm of Hg. The product analysis was 17.6% Al, 12.5% Zr, 15.0% Cl, and 8.3% glycine.

EXAMPLE IV

Magnesium glycinate was prepared by reacting 4 grams of glycine with 2.5 grams of basic magnesium carbonate (26.3% Mg) in 30 grams of water while agitating at 75° C. for one half hour. The cooled mixture was then added to 77 grams of zirconyl chloride (13.6% Zr) with stirring. To the above solution 100 grams of 50% aluminum chlorhydroxide (12.5% Al) was added with agitation. The mixture was heated at 85° C. for 20 minutes. The product was then evaporated at 53° C. under a vacuum of 200 mm of Hg and contained 15.8% Al, 13.6% Mg. 5.3% glycine and 22.1% Cl.

EXAMPLE V

Calcium glycinate was prepared by mixing 2 grams of glycine with 1.32 grams of calcium carbonate powder in 10 grams of water with agitation. The mixture was heated at 85° C. for 30 minutes. Five grams of 5/6 basic aluminum bromide powder, $Al_2(OH)_5Br$ (20.5% Al) was dissolved in 20 grams of water and then added to 79 grams of zirconyl hydroxybromide, ZrO(OH)Br (17.5% Zr). The calcium glycinate slurry was then added hot to the resultant mixture with agitation. The solution was heated at 65° C. for 1 hour and then tray dried at 50° C. under a vacuum of 175 mm of Hg. The product contained 2.24% Al, 31.2% Zr, 4.26% glycine, 28.6% Br and 1.10% Ca.

EXAMPLE VI

Sodium glycinate was prepared by reacting 3 grams of glycine with 3.2 grams of 50% sodium hydroxide in 10 grams of water while stirring at 50° C. for 15 minutes. Ten grams of 5/6 basic aluminum nitrate powder $Al_2(OH)_5NO_3$ (22.8% Al) was dissolved in 50 grams of water and then added to 60 grams of a zirconyl bromide solution, $ZrO\ Br_2$ (12.8% Zr). On addition of the sodium glycinate solution to the above a precipitate formed which redissolved with agitation at 50° C. for 20 minutes. The solution was oven dried at 70° C. under a vacuum of 175 mm of Hg. The product contained 5.91% Al, 19.2% Zr, 6.56% $NO_3$, 31.8% Br, 2.96% Na, and 6.34% glycine.

EXAMPLE VII

Potassium valinate was prepared by dissolving 2 grams of L-(+)-valine in 100 grams of water. To the solution was added 0.94 grams of potassium hydroxide pellets while agitating at 50° C. for 15 minutes. Thirty grams of 3⅓% zirconyl hydroxychloride (14.1% Zr) was then added to 100 grams of 50% aluminum chlorhydroxide (12.5% Al) with stirring. Addition of the potassium valinate solution to the above resulted in the formation of a precipitate which redissolved on heating at 50° C. for 30 minutes with agitation. The clear solution was evaporated at 65° C. under a vacuum of 175 mm of Hg. The product contained 21.4% Al, 7.66% Zr, 17.6% Cl, 1.20% K. and 3.6% glycine.

EXAMPLE VIII

Ammonium glycinate was prepared by dissolving 5.6 grams of glycine in 10 grams of water and adding to this 4.4 grams of 28–30% ammonium hydroxide with agitation. Five grams of 5/6 basic aluminum nitrate (22.8% Al) was dissolved in 10 grams of water and then added to 97 grams of a zirconyl nitrate solution, $ZrO\ (NO_3)_2$ (7.9% Zr). Addition of the ammonium glycinate solution to the above mixture resulted in the formation of a precipitate which redissolved with agitation on warming up to 35° C. for 15 minutes. The solution was oven dried at 80° C. under a vacuum of 252 mm of Hg. The product analyzed 3.4% Al, 22.2% Zr, 42.2% $NO_3$, 2.54% $NH_4$, and 11.9% glycine.

EXAMPLE IX

Magnesium glycinate was prepared by reacting 5 grams of glycine with 3.1 grams of basic magnesium carbonate (26.3% Mg) in 15 grams of water. The mixture was heated at 75° C. for ½ hour with agitation. The hot solution was then added to 113 grams of zirconyl nitrate (7.9% Zr) with stirring. After the addition of 1.5 grams of aluminum hydroxide powder (28.8% Al), the mixture was reacted with agitation at 75° C. for ½ hour. To the resultant clear solution was added 7.9 grams of ⅔ basic aluminum sulfate, $Al(OH)_2SO_4$ (3.1% Al). The solution was then oven dried at 58° C. under a vacuum of 328 mm of Hg. The product contained 1.2% Mg, 13.2% glycine, 1.5% Al, 24.3% Zr, 4.02% $SO_4$ and 29.5% nitrate.

EXAMPLE X

Magnesium β-alaninate was prepared by reacting 4.86 grams of β-alanine with 2.5 grams of basic magnesium carbonate (26.3% Mg) in 25 grams of water. The mixture was heated at 75° C. with agitation for one half hour. The hot solution was added to 100 grams of zirconyl hydroxybromide solution (17.5% Zr). To the resultant solution was added 14.2 grams of ⅔ basic aluminum sulfamate, $Al(OH)_2(OSO_2NH_2)$ (9.19% Al, see U.S. Pat. No. 2,765,213 by S. M. Beekman) with agitation. The solution was evaporated at 60° C. under a vacuum of 252 m of Hg. The product contained 1.8% Al, 30.9% Zr, 0.53 Mg, 5.91% β-alanine and 5.3% sulfamates.

EXAMPLE XI

Monohydroxyaluminum glycinate was prepared by reacting 2 grams of glycine with 1.25 grams of aluminum hydroxide (28.8% Al) powder in 10 grams of water. The mixture was agitated at 75° C. for ½ hour. To 15 grams of a 33½ solution of 5/6 basic aluminum iodide solution, $Al_2(OH)_5I$ (5.49% Al), was added 31.2 grams of a zirconyl iodide solution (6.3% Zr). The glycinate mixture was then added to the above solution while agitating at 80° C. for 30 minutes. The resultant clear solution was evaporated at 55° C. under a vacuum of 150 mm of Hg. The product contained 6.63% Al, 11.1% Zr, 48.3% I, and 11.1% glycine.

EXAMPLE XII 0.2 parts by weight of $Al(OH)_3$—$Mg(OH)_2$—Glycine complex containing 13.4% Al; 6.9% Mg; and 26.7% glycine prepared as per U.S. Pat. No. 3,208,906 were added to 13.7 parts by weight of ZrO(OH)Cl solution containing 13.3% Zr — causing a rise in pH from 0.45 to 1.20. This solution was then slowly added to 77.9 parts by weight of aluminum chlorhydrate ($Al_2(OH)_5Cl$) solution containing 4.16% Al. A water-white soluton with a pH = 3.5 was obtained, which was then oven-dried at 65° C. for 40 hours. A light yellow crystalline solid was obtained, yielding the following assay:

Al — 18.5%
Zr — 10.8%
Al:Zr mol ratio — 5.8:1
Mg — 0.08%
Glycine — 0.34%
*pH of 15% w/w solution — 3.3
*Reconstituted 15% solution — Clear
*15 weight percent $ZrO_2 + Al_2O_3$ aqueous solution.

EXAMPLE XIII 0.4 parts by weight of an $Al(OH)_3$—$MgCO_3$—Glycine complex containing 9.0% Al; 9.0% Mg; and 27.0% glycine prepared as per U.S. Pat. No. 3,208,906 were added to 41.7 parts by weight of ZrO(OH)Cl solution containing 13.3% Zr causing a rise in pH from 0.45 to 0.80. This solution was then slowly added to 62.3 parts by weight of aluminum chlorhydrate ($Al_2(OH)_5Cl$) solution containing 1.31% Al. A water-white solution with a pH = 1.75 was obtained which was then oven-dried at 65° C. for 40 hours.

A yellow crystalline solid was obtained, yielding the following assay:

Al — 5.1%
Zr — 33.3%
Al:Zr mol ratio — 0.5:1
Mg — 0.20%
Glycine — 0.65%
*pH of 15% w/w solution — 3.4
*Reconstituted 15% solution — Slightly turbid
*15 weight percent $ZrO_2$ + $Al_2O_3$ aqueous solution.

EXAMPLE XIV 0.2 parts by weight of $Al(OH)_3$—$MgSi_3O_8$—Glycine codried complex containing 5.6% Al; 7.1% Mg; 26.1% Si; and 27.3% glycine prepared as per U.S. Pat. No. 3,208,906 were added to 20.8 parts by weight $ZrOCl_2$ solution containing 13.2% Zr and the resultant cloudy solution heated to and held at 70° C. for 4 hours.

The cloudy solution was then slowly added to 47.3 parts by weight of aluminum chlorhydrate ($Al_2$-$(OH)_5Cl$) solution containing 3.43% Al. A turbid solution with a pH = 2.7 was obtained, which was then oven-dried at 65° C. for 40 hours. A yellow crystalline solid was obtaind yielding the following assay:

Al — 10.9%
Zr — 18.0%
Al:Zr — 2.1:1.0
Mg — 0.12%
Glycine — 0.46%
pH of 15% w/w solution — 3.7
Reconstituted 15% solution — Cloudy

EXAMPLE XV 0.3 parts by weight of $Al(OH)_3$—$Mg(OH)_2$ glycine codried complex containing 13.4% Al; 6.9% Mg; and 26.7% glycine prepared as per U.S. Pat. No. 3,208,906 were added to 22.4 parts by weight ZrO(OH)Cl solution containing 13.3% Zr causing a rise in pH from 0.45 to 1.40. This solution was then slowly added to 85.8 parts by weight of 5/6 basic aluminum bromide complex ($Al_2(OH)_5Br$) solution containing 3.10% Al. A slightly opalescent solution with a pH = 3.6 was obtained which was then oven-dried at 65° C. for 24 hours. A tannish yellow crystalline solid was obtained, yielding the following assay:

Al — 12.6%
Zr — 14.8%
Al:Zr — 2.9:1.0
Mg — 0.12%
Glycine — 0.51%
pH of 15% w/w solution — 3.9
Reconsituted 15% solution — Slightly tannish tint

EXAMPLE XVI 7.5 gm of powdered 5/6 basic aluminum chlorhydroxide (Reheis' Chlorhydrol Micro-Dry Powder) containing 25% aluminum was dissolved in 20 gm of water. To 90.8 gm of a 30% zirconyl chloride solution (13.6% Zr) was added 10 gm of dihydroxy aluminum glycinate (Chattem Chemical Company; 16.8% Al, 48.7% glycine), while agitating at 75° C. for 20 minutes. The above mixture was added to the chlorhydroxide solution with stirring. The final solution was oven-dried at 55° C. under vacuum of 303 mm Hg. The product contained 6.7% Al, 23.0% Zr, 8.9% glycine, and 20.4% Cl.

Among the advantages of the complexes of the present invention is the fact that the amino acid salts or derivatives are more basic and better buffers than the simple amino acids themselves. This is due to the fact that most of the derivatives of alkali and alkaline earth metals, particularly those which are insoluble in water, are hydroxylated. Since the formation of complexes of the present invention results in increasing the pH of the highly acid zirconium systems, the more basic amino acid salts and derivatives can be used in smaller amounts to achieve the necessary pH levels for antiperspirant use. In addition, as a result of using the amino acid salts and derivatives, other ions known for their anti-perspirant activity as well as their basic character are introduced into the astringent complexes of the present invention. For example, the use of dihydroxy aluminum glycinate results in the addition of more aluminum which is well known for its anti-perspirant activity.

As indicated previously, the complexes of the present invention may be used in a variety of conventional anti-perspirant forms which are applied to the human axilla for effective perspiration inhibition. In such formulations, the complex should be present in such amounts that the total aluminum plus zirconium content of the formulation is between about 1.5 and 15 weight percent (depending on the type of formulation employed), calculated as the oxides of the aluminum and zirconium.

For example, aqueous solutions of the complexes may be used in lotions, oil/water creams, and co-dispensing aerosols. The complexes of the present invention are not as a rule soluble in pure alcoholic solvent systems. However, the complexes may be considered for use in hydro-alcoholic mixed solvents, such as 75 percent ethanol and 25 percent water. In either the aqueous solutions or the hydro-alcoholic solvents, the complexes of the present invention should be present in the above anti-perspirant forms in amounts such that the total content of aluminum plus zirconium in the formulation is on the order of about 5 to 15 weight percent (calculated as the oxides of aluminum and zirconium) or 10 to 30 weight percent of the active ingredient (calculated on a solids basis).

The complexes of the present invention may also be used in the now popular powder-in-oil aerosol sprays. The powder-in-oil systems comprise the dispersion of a finely divided anti-perspirant powder, such as the dried complexes of the present invention, in a non-solubilizing polar organic liquid such as an ester which serves as both a dispersion medium as well as a emollient. The organic liquid coats or wets the powder particles to render them heavier and more occlusive and/or substantive to the axillary region. This primary powder-in-oil suspension, known as the "concentrate," may also include a suspending or anti-compaction agent such as Cab-O-Sil or Bentone 34, to inhibit the dispersed phase from settling and compacting irreversibly. The so-called "extra-dry" formulations use less emollient and higher levels of dry powder, such as talc. Finally, after dynamic agitation the viscous concentrate is generally mixed with about 9 times its weight of a blend of standard propellants.

When used in the powder-in-oil aerosol sprays, the complexes of the present invention should be present in the finished formulation to the extent of about 1 to 6 weight percent, and preferably about 1.5 to 3 weight percent, total aluminum plus zirconium, calculated as the oxides. A typical powder-in-oil aerosol suspension would employ about 5 percent w/w of the active ingredient (dried complex) or about 2.5 percent total oxides.

Typical anti-perspirant formulations employing the complexes of the present invention are exemplified in Table I.

The present invention may be embodied in other specific forms without departing from the spirit or essential attributes thereof and, accordingly, reference should be made to the appended claims, rather than to the foregoing specification as indicating the scope of the invention.

TABLE I

ANTIPERSPIRANT FORMULATIONS

| | Parts By Weight | | | | |
|---|---|---|---|---|---|
| | A | B | C | D | E |
| Ingredient | Powder-in-oil aerosol | Powder-in-Oil extra-dry aerosol | Spray: (Manual-Pump) | Oil-in-water lotion | Oil-in-water cream |
| Active Ingredient (Antiperspirant) | | | | | |
| Complex of Example I | 3.5 | | | | |
| Complex of Example XV | | | 10.0 | | |
| Complex of Example IV | | 5.0 | | | |
| Complex of Example XII | | | | 18.0 | 15.0 |
| Isopropyl Myristate | 6.0 | 3.0 | | | |
| Cab-O-Sil M-5 (1) | 0.3 | 0.5 | | | |
| Perfume | 0.2 | | 0.5 | q.s. | q.s. |
| Propylene Glycol | | | 15.0 | | |
| Propellant 11 | 45.0 | 45.0 | | | |
| Propellant 12 | 45.0 | 45.0 | | | |
| Water | | | 39.5 | 66.0 | 56.0 |
| Alcohol SD-39C | | | 35.0 | | |
| Talc, U.S.P. | | 1.5 | | | |
| Arlacel 165 (4) | | | | | 18.0 |
| Amerchol L-101 (2) | | | | 5.0 | |
| Solulan 98 (2) | | | | 2.0 | |
| Myrj 52 (4) | | | | 4.0 | |
| Cetyl Alcohol | | | | 2.0 | |
| Glycerin | | | | 2.0 | 5.0 |
| Veegum HV (3) | | | | 1.0 | |
| Preservative | | | | q.s. | q.s. |
| Spermaceti | | | | | 5.0 |
| Titanium Dioxide | | | | | 1.0 |

(1) Cab-O-Sil M-5 - fumed amorphous silica of Cabot Corp.
(2) Amerchol L-101 and Solulan 98 - lanolin derivatives of Amerchol, Inc.
(3) Veegum HV - product of R. T. Vanderbilt & Co.
(4) Arlacel 165 and Myrj 52 - non-ionic emulsifiers of ICI America, Atlas Chem. Div.

I claim:

1. An astringent, water soluble complex formed by reacting in an aqueous solution:
   a. a basic aluminum compound selected from the group having the general empirical formula:

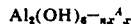
   $Al_2(OH)_{6-nx}A_x$ wherein $x$ may vary from greater than 0 to less than 6, $6-nx$ is greater than or equal to 0, $n$ is the valence of $A$, and $A$ is selected from the group consisting of halides, nitrate, sulfamate, sulfate and mixtures thereof;
   b. a zirconium compound selected from the group having the general empirical formula:

   $ZrO(OH)_{2-nz}B_z$ wherein $z$ may vary from 0.9 to 2, $n$ is the valence of B, $2-nz$ is greater than or equal to 0, and $B$ is selected from the group consisting of halides, nitrate, sulfamate, sulfate and mixtures thereof; and
   c. an amino compound selected from alkaline salts of amino acids, said alkaline salts of amino acids being derived from amino acids in which the number of a amino groups is equal to the number of carboxyl groups in the molecule; said zirconium and basic aluminum compounds being present in such amounts as to yield an Al/Zr mole ratio of about 10:1 to 1:10, and said amino compound being present in such an amount that the pH of a 5 to 15 weight percent (based on the oxides of Al and Zr) aqueous solution of the complex is at least about 3.

2. An astringent complex according to claim 1 wherein x varies from about 1 to about 2.

3. An astringent complex according to claim 1 wherein A is chloride.

4. An astringent complex according to claim 1 wherein the basic aluminum compound is a phenosulfonate complex of said basic aluminum compound.

5. An astringent complex according to claim 1 wherein B is chloride and z is about 1.

6. An astringent complex according to claim 1 wherein B is chloride and z is about 2.

7. An astringent complex according to claim 1 wherein said alkaline salts are derived from amino acids selected from the group consisting of glycine, β-alanine, DL-valine, arginine, L-(−)-proline, and mixtures thereof.

8. An astringent complex according to claim 1 wherein the amino compound is an alkaline salt in which the cation is selected from the group consisting of sodium, potassium, ammonium, magnesium, calcium and mixtures thereof.

9. An astringent complex according to claim 1 wherein the Al/Zr mole ratio is about 1:1 to 4:1.

10. An astringent complex according to claim 1 wherein said complex also includes aluminum chloride.

11. An astringent complex according to claim 1 wherein said complex is in the form of a powder.

12. An astringent complex according to claim 1 wherein said amino compound is sodium glycinate.

13. An antiperspirant composition comprising an aqueous solution of the complex according to claim 1 wherein said complex is present in an amount such that the total amount of aluminum plus zirconium in the solution, calculated as the oxides, is about 5 to 15 weight percent.

14. A powder-in-oil antiperspirant composition comprising an aerosol propellant and the complex according to claim 11 wherein said complex is present in an amount such that the total aluminum plus zirconium present in the antiperspirant composition, calculated as the oxides, is about 1–6 weight percent.

15. A process for making an astringent, water soluble aluminum-zirconium complex comprising reacting in an aqueous solution:

a. a basic aluminum compound selected from the group having the general empirical formula:

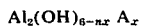

$$Al_2(OH)_{6-nx} A_x$$

wherein $x$ may vary from greater than 0 to less than 6, $6-nx$ is greater than or equal to 0, $n$ is the valence of A, and A is selected from the group consisting of halides, nitrate, sulfamate, sulfate and mixtures thereof;

b. a zirconium compound selected from the group having the general empirical formula:

$$ZrO(OH)_{2-nz} B_z$$

wherein $z$ may vary from 0.9 to 2, $n$ is the valence of B, $2-nz$ is greater than or equal to 0, and B is selected from the group consisting of halides, nitrate, sulfamate, sulfate and mixtures thereof; and c. an amino compound selected from alkaline salts of amino acids and hydroxy aluminum salts of amino acids, said alkaline and hydroxy aluminum salts of amino acids being derived from amino acids in which the number of amino groups is equal to the number of carboxyl groups in the molecule; said zirconium and basic aluminum compounds being reacted in such amounts as to yield an Al/Zr mole ratio of about 10:1 to 1:10, and said amino compound being reacted in such an amount that the pH of a 5 to 15 weight percent (based on the oxides of Al and Zr) aqueous solution of the complex is at least about 3.

16. A process according to claim 15 wherein the amino compound is an alkaline salt in which the cation is selected from the group consisting of sodium, potassium, ammonium, magnesium, calcium and mixtures thereof.

17. A process according to claim 15 wherein the amino compound is a hydroxy aluminum salt selected from the group consisting of dihydroxy aluminum glycinate, monohydroxy aluminum glycinate, aluminum-magnesium-hydroxy-glycine compounds, and mixtures thereof.

18. A process according to claim 15 wherein the Al/Zr mole ratio is about 1:1 to 4:1.

19. A process according to claim 15 wherein aluminum chloride is also added in the reaction.

20. A process according to claim 15 wherein the reaction solution is dried to a powder.

* * * * *